United States Patent [19]

Elbrecht et al.

[11] Patent Number: 5,162,337
[45] Date of Patent: Nov. 10, 1992

[54] ANIMAL GROWTH PROMOTION

[75] Inventors: Alexander Elbrecht, Watchung; Yi-Tien Yang, Somerville; Roy G. Smith, Westfield, all of N.J.

[73] Assignee: Merck & Co., Inc., N.J.

[21] Appl. No.: 593,439

[22] Filed: Oct. 5, 1990

[51] Int. Cl.$^5$ .................. A61K 31/44; A61K 31/56; A61K 31/55; A61K 31/495; A61K 31/505; A61K 31/415

[52] U.S. Cl. .................. 514/300; 514/177; 514/179; 514/214; 514/255; 514/256; 514/396; 514/252

[58] Field of Search ............ 514/177, 179, 214, 252, 514/256, 255, 300, 396

[56] References Cited

U.S. PATENT DOCUMENTS

| | | | |
|---|---|---|---|
| 4,273,782 | 6/1981 | Cross et al. | 514/252 |
| 4,322,416 | 3/1982 | Metcalf et al. | 514/179 |
| 4,617,307 | 10/1986 | Browne | 514/300 |
| 4,620,007 | 10/1986 | Grohe et al. | 514/300 |
| 4,728,645 | 3/1988 | Browne | 514/214 |
| 4,757,061 | 7/1988 | Faustini et al. | 514/177 |
| 4,757,082 | 7/1988 | Hirsch et al. | 514/396 |
| 4,762,836 | 8/1988 | Hirsch | 514/256 |
| 4,764,376 | 8/1988 | Hirsch et al. | 514/255 |

FOREIGN PATENT DOCUMENTS

| | | |
|---|---|---|
| 0293978 | 12/1988 | European Pat. Off. |
| 0296749 | 12/1988 | European Pat. Off. |
| 0316097 | 5/1989 | European Pat. Off. |

*Primary Examiner*—Frederick E. Waddell
*Assistant Examiner*—K. Weddington
*Attorney, Agent, or Firm*—Raymond M. Speer; Jack L. Tribble; Gerard H. Bencen

[57] ABSTRACT

Female prenatal, neonatal and postnatal animals are treated with compositions containing steroid biosynthesis inhibitors or antagonists which prevents the conversion of androgens to estrogens. The compositions are useful for improving growth and feed efficiency.

4 Claims, No Drawings

ANIMAL GROWTH PROMOTION

BACKGROUND OF THE INVENTION

The ability to increase the rate of growth and efficiency of food utilization of female animals to levels which correspond to those of normal intact male animals would have a significant impact on meat production. Attempts have been made to improve post-natal female growth by pre-natal manipulation of sexual differentiation. Pre-natal treatment with testosterone propionate followed by post-natal treatment with testosterone propionate and estradiol benzoate of heifer calves produced an additive improvement in growth rate, feed efficiency and carcass merit of heifers, DeHaan et al., J. Anim. Sci. 68: 2198–2207 (1990). Ewes exposed to testosterone between days 30 and 80, 50 and 100 or 70 and 120 of fetal life failed to show regular overt oestrous cycles, although some of the ewes ovulated. Prenatal androgenization, treatment with testosterone, has been shown to enhance ewe production efficiency by improving growth rate, feed efficiency and carcass merit, DeHaan et al., J. Amin. Sci. J. Anim. Sci. 65 (suppl. 1): 85 (1987). In utero treatment with testosterone propionate resulted in ewes with increased weight gain and feed efficiency along with lower fat, Jenkins et al., J. Anim. Sci. (suppl. 1) 65: 248 (1987). Exposure to testosterone propionate in utero resulted in gilts gaining weight at a higher level between day 28 and 125 but did not shown an increase in feed efficiency, Matulis et al., J. Anim. Sci. 65 (suppl. 1): 249 (1987). Female rats treated perinatally with testosterone propionate exhibited increased growth and efficiency of food utilization when compared to non-treated controls, Perry et al., J. Endocr. 81: 35–48 (1979).

The ability of males to grow at a rate higher than females generally becomes more evident at or after puberty suggesting that the difference may be due, at least in part, to the influence of sex steroids, Jansson et al., Endocrin. 114: 1287–1294 (1984). Gonadectomy of male and female rats results in a decrease in male growth and an increase in the growth of females, Weidemann, In: Daughaday (ed) Endocrine Control of Growth. Elsevier, New York, p. 67 (1981). Circulating estrogen suppresses somatic growth while testosterone is required for male type growth, Jansson et al., Endocrin. 114: 1287–1294 (1984). The sites of action on growth appears to be different for estrogen and for androgen, Jansson et al., Am. J. Physiol. 244: Ei35–Ei140 (1983).

OBJECTS OF THE INVENTION

It is accordingly, an objective of the present invention to provide a means of enhancing weight gain and feed efficiency in mammals. Another object is to treat prenatal, neonatal and postnatal mammals with steroid biosynthesis inhibitors or antagonists to prevent the conversion of testosterone to estradiol. A further object is to treat mammals with an aromatase inhibitor to inhibit the conversion of androgens to estrogens and to modify the hypothalamic/pituitary/gonadal axis.

SUMMARY OF THE INVENTION

Female prenatal, neonatal and postnatal animals are treated with compositions containing steroid biosynthesis inhibitors or antagonists which prevents the conversion of androgens to estrogens. The compositions are useful for improving growth and feed efficiency.

DETAILED DESCRIPTION OF THE INVENTION

The present invention relates to the use of estrogen synthesis inhibitors which prevent the conversion of androgens (testosterone, androstenedione) to estrogens (estradiol, estrone), particularly aromatase inhibitors, to enhance growth and feed efficiency in meat animals. Meat animals as used herein includes, but is not limited to, cattle, swine, sheep, goats, horses, buffalo and any mammal which may be domesticated and/or raised for use as a meat protein source. Animal as used herein is intended to include only meat animals or mammals and does not include birds or fish.

The animals are treated with a composition containing an aromatase inhibitor to prevent the conversion of testosterone to estradiol. The treatment may be administered to prenatal, neonatal and postnatal animals with the objective of modifying the hypothalamic/pituitary/gonadal axis. Aromatase is an enzyme complex incorporating a NADPH-cytochrome c-reductase and a cytochrome $P_{450}$ component which mediates the conversion of androgens to estrogens, Bellino, J. Steroid Biochem. 17: 261–270 (1982). The reaction is believed to involve three hydroxylation steps, two at the C-19 position (Meyer, Biochem. Biophys. Acta 17: 441–442 [1955]; Morato et al., Biochem. Biophys. Res. Comm. 6: 334–338 [1961]) and one at C-2 (Hahn and Fishman, J. Biol. Chem. 259: 1689–1694 [1984]; Brodie et al., J. Am. Chem. Soc. 91: 1241–1242 [1969]) which result in the conversion of the A ring of the androgen molecule to an aromatic ring. Since aromatization is a unique reaction in the biosynthesis of estrogens, specific inhibitors should not cause deprivation of other essential steroids. An aromatase inhibitor as defined herein is any steroidal or non-steroidal compound which prevents the conversion of androgens to estrogens. The compounds include substrate analogues of androstenedione, testosterone or other steroidal substances involved in the aromatase pathway, Henderson, J. Steroid Biochem. 27: 905–914 (1987). Non-steroidal compounds that block aromatase activity are also included within the scope of the invention. These non-steroidal compounds include compounds or analogues that can bind to the enzymatic active site of aromatase and inhibit enzymatic activity. Non-steroidal or steroidal compounds will also include compounds or analogues that bind to the enzyme at a site away from the enzymatic active site and cause a structural change in the enzyme which results in a loss of enzymatic activity. Aromatase inhibitors further include non-steroidal compounds that interfere with cytochrome $P_{450}$ mediated hydroxylations such as those described by Brodie et al., J. Steroid Biochem. 27: 899–903 (1987). Aromatase inhibitors are known for the treatment of estrogen-dependent diseases such as breast cancer.

The following compounds are known aromatase inhibitors as disclosed by the associated reference. The reference will also directly contain a method for making the compound or will direct one who wishes to use the compound to a method for producing the compound. The aromatase inhibitors of the instant invention include, but are not limited to, the following compounds: 6-[(1H-imidazol-1-yl)phenylmethyl]-1 methyl-1H-benzotriazole, 6-[(4-chlorophenyl)(1H-1,2,4-triazol-1-yl)methyl]-1-methyl-1H-benzotriazole as described in Publication No. 293,978; 2,2-[5-(1H-1,2,4-triazol-1-ylmethyl)-1,3-phenylene]di(2-methylpropiononitrile), 2,2-[5-(imidazol-1-ylmethyl)-1,3-phenylene]-di(2-methylpropionitrile), 2-[3-(1-hydroxy-1-methylethyl)-5-(1H-1,2,4-triazol-1-ylmethylphenyl]-2-methylpropiononitrile, 2,2-[5-dideuterio(1H-1,2,4-triazol-1-yl)methyl-1,3-phenylene]di(2trideuteriomethyl-3,3,3-(trideuteriopropiononitrile), and 2,2-[5-dideuterio(1H-1,2,4-triazol-1-ylmethyl-1,3-phenylene)di(2-methylpropiononitrile) as disclosed in European Patent Application, Publication No. 296,749; 1,1-dimethyl-8-(1H-1,2,4-triazol-1-ylmethyl)-2(1H)-naphtho[2,1-b]furanone, 1,2-dihydro-1,1-dimethyl-2-oxo-8-(1H-1,2,4-triazol-1-ylmethyl)naphtho-[2,1-b]furan-7-carbonitrile, 1,2-dihydro-1,1-dimethyl-2-oxo-8-(1H-1,2,4-triazol-1-ylmethyl)-naphtho[2,1-b]furan-7-carboxamide, and 1,2-dihydro-1,1-dimethyl-2-oxo-8-[di(1H-1,2,4-triazol-1-yl)methyl]-naphtho[2,1-b]furan-7-carbonitrile as disclosed in European Patent Application, Publication No. 316,097; 2-(4-chlorobenzyl)-2-fluoro-1,3-di(1,2,4-triazol-1-yl)propane, 2-fluoro-2-(2-fluoro-4-chlorobenzyl)-1,3-di(1,2,4-triazol-1-yl)propane, 2-fluoro-2-(2-fluoro-4-trifluoromethylbenzyl)-1,3-di(1,2,4-triazol-1-yl)propane, 3-(4-chlorophenyl)-1-(1,2,4-triazol-1-yl)-2-(1,2,4-triazol-1-ylmethyl)butan-2-ol, 2-(4-chloro-α-fluorobenzyl)-1,3-di(1,2,4-triazol-1-yl)propan-2-ol, 2-(4-chlorobenzyl)-1,3-bis(1,2,4-triazol-1-yl)propane, 4-[2-(4-chlorophenyl)-1,3-di(1,2,4-triazol-1-ylmethyl)ethoxymethyl]-benzonitrile, 1-(4-fluorobenzyl)-2-(2-fluoro-4-trifluoromethylphenyl)-1,3-di(1,2,4-triazol-1-yl)propan-2-ol, 2-(4-chlorophenyl)-1-(4-fluorophenoxy)-1,3-di(1,2,4-triazol-1-yl)propan-2-ol, 1-(4-cyanobenzyl)-2-(2,4-difluorophenyl)-1,3-di(1,2,4-triazol-1-yl)propan-2-ol and 2-(4-chlorophenyl)-1-phenyl-1,3-di(1,2,4-triazol-1-yl)-propan-2-ol as described in European Patent Application, Publication No. 299,684; 5-bis(4-chlorophenyl)-methylpyrimidine as disclosed in U.S. Pat. No. 4,762,836; α,α-bis(4-chlorophenyl)-2-pyrazinemethanol as described in U.S. Pat. No. 4,764,376; N-(2,4-difluorophenyl)-N-benzyl-3-pyridinemethanamine and N-(2-chlorophenyl-α-(4-fluorophenyl)-3-pyridinemethanamine as disclosed in U.S. Pat. No. 4,744,251; 1-(10,11-dihydro-5H-dibenzo[a,d]cyclohepten-5-yl)-1H-imidazole and 1-(9H-fluoren-9-yl)-1H-imidazole as disclosed in U.S. Pat. No. 4,757,082; 3-bis(4-chlorophenyl)-3-methylpyridine and α,α-bis(4-chlorophenyl)-3-pyridinemethanol as disclosed in U.S. Pat. No. 4,757,076; 5H-5-(4-cyanophenyl)-6,7-dihydropyrrolo[1,2-c]imidazole and 5H-5-(4-cyanophenyl)-6,7,8,9-tetrahydroimidazo[1,5-a]azepine and disclosed in U.S. Pat. No. 4,728,645; 5-[(1H-imidazol-1-yl)phenylmethyl]-2-methyl-1H-benzimidazole and 5-[(3-chlorophenyl)(1H-imidazol-1-yl)-methyl]-1H-benzimidazole as disclosed in European Patent Application, Publication No. 260,744; (Z)-α-(1,2,4-triazol-1-ylmethyl)stilbene-4,4'-dicarbonitrile, (Z)-4'-chloro-α-(1,2,4-triazol-1-ylmethyl)stilbene-4-carbonitrile, (Z)-α-(1,2,4-triazol-1-ylmethyl)-4'-(trifluoromethyl)stilbene-4-carbonitrile, (E)-β-fluoro-α-(1,2,4-triazol-1-ylmethyl)stilbene-4,4'-dicarbonitrile, (Z)-4'-fluoro-α-(imidazol-1-ylmethyl)-stilbene-4-carbonitrile, (Z)-2',4'-dichloro-α-(imidazol-1-ylmethyl)stilbene-4-carbonitrile, (Z)-4'-chloro-α-(imidazol-1-ylmethyl)stilbene-4-carbonitrile, (Z)-α-(imidazol-1-ylmethyl)stilbene4,4'-dicarbonitrile, (Z)-α-(5-methylimidazol-1-ylmethyl)stilbene-4,4'-dicarbonitrile, and (Z)-2-[2-(4-cyanophenyl)-3-(1,2,4-triazol-1-yl)propenyl]pyridine-5-carbonitrile as disclosed in European Patent Application, Publication No. 299,683; (1R*,2R*)-6-fluoro-2-(4-fluorophenyl)-1,2,3,4-tetrahydro-1-(1H-1,2,4-triazol-1-ylmethyl)naphthalene, (1R*,2R*)-6-fluoro-2-(4-fluorophenyl)-1,2,3,4-tetrahydro-1-(1H-imidazolylmethyl)-naphthalene, (1R*,2R*)- and (1R*,2S*)-2-(4-fluorophenyl)-1,2,3,4-tetrahydro-1-(1H-1,2,4-triazol-1-ylmethyl)naphthalene-6-carbonitrile, (1R*,2R*)- and (1R*,2S*)-2-(4-fluorophenyl)-1,2,3,4-thetahydro-1-(1H-imidazolylmethyl)naphthalene-6-carbonitrile, (1R*,2R*)- and (1R*,2S*)-1,2,3,4-tetrahydro-1-(1H-1,2,4-triazol-1-ylmethyl)naphthalene-2,6-dicarbonitrile, (1R*,2R*)- and (1R*,2S*)-1,2,3,4-tetrahydro-1-(1H-imidazol-1-ylmethyl)naphthalene-2,6-dicarbonitrile, and (1R*,2S*)-2-(4-fluorophenyl)-1,2,3,4-tetrahydro-1-(5-methyl-1H-imidazolylmethyl)-naphthalene-6-carbonitrile as disclosed in European Patent Application, Publication No. 281,283; 8-chloro-5-(4-chlorophenyl)-5H-indeno[1,2-d]pyrimidine as disclosed in U.S. Pat. No. 4,769,378; 5-bis (4-chlorophenyl)methylpyrimidine as disclosed in U.S. Pat. No. 4,762,836; 10-(2-propynyl)-estr-4-ene-3,17-dione as disclosed in U.S. Pat. No. 4,322,416; 6-[(4-chlorophenyl)(1H-1,2,4-triazol-1-yl)methyl]-1-methyl-1H-benzotriazole as described in European Patent Application, Publication No. 293,978; 1-methylandrosta-1,4-dien-3,17-dione as disclosed in U.S. Pat. No. 4,591,585; 3-ethyl-3-(4-pyridyl)piperidine-2,6-dione as disclosed in British Patent GB 2,151,226; 4-hydroxyandrostene-3,17-dione as disclosed in U.S. Pat. No. 4,500,523; 4-(5,6,7,8-tetrahydroimidazo[1,5-a]pyridin-5-yl)benzonitrile as disclosed in U.S. Pat. No. 4,728,645; 6-methyleneandrosta-1,4-diene-3,17-dione, 4-aminoadrostan-1,4,6-trien-3,17-dione and 4-aminoandrosta-4,6-diene-3,17-dione as disclosed in U.S. Pat. No. 4,757,061; 3-(1H-imidazol-1-ylmethyl)-2-methyl-1H-indole-1-propanoic acid as disclosed in U.S. Pat. No. 4,273,782; 5-[3-chlorophenyl)(1H-imidazol-1-yl)methyl]-1H-benzimidazole as disclosed in European Patent Application, Publication No. 260,744; 10β-thiiranylestr-4-ene-3,17-dione and 10β-oxiranylestr-4-ene-3,17-dione as disclosed in J. Organ. Chem. 53: 5947–5951 (1988); 3-ethyl-3-(4-pyridyl)-piperidine-2,6-dione as described in U.S. Pat. No. 4,668,689; 3-(4-aminophenyl)-3-ethylpyrrolidine-2,5-dione as disclosed in J. Med. Chem. 29: 520–523 (1986); 1-(7-carboxyheptyl)-imidazole as described in U.S. Pat. No. 4,320,134; 1,1-dimethyl-8-(1H-1,2,4-triazol-1-ylmethyl)-2 (1H)-naphtho[2,1-b]furanone (1a) as disclosed in European Patent Application, Publication No. 316,097; ±5-(p-cyanophenyl)-5,6,7,8-tetrahydroimidazo[1,5-a]pyridine hydrochloride as disclosed in U.S. Pat. No. 4,617,307; 1,4,6-androstatriene-3,17-dione disclosed in Biochem. Pharmac. 31: 2017–2023 (1982) and other compounds well known in the art of aromatase inhibition and cancer therapy such as bis-(p-cyanophenyl)-imidazo-1-yl-methane hemisuccinate and pharmaceutically acceptable derivatives, acid addition salts and possible stereochemically isomeric forms thereof, if and where appropriate. The invention is also intended to include any biologically active equivalents of an aromatase inhibitor as described above.

The novel compositions of this invention include one or more of the aromatase inhibitors and are administered either orally or parenterally. The term aromatase inhibitor as used herein is intended to include one or more aromatase inhibitor compounds. Parenteral administration may be by intraveneous, subcutaneous or intraperitoneal injections or by implants. Implants as used herein will generally consist of timed release formulations which will allow administration of the composition for various lengths of time. Administration of the composition may be by a single dose or multiple doses, or continuous administration depending on the levels required to inhibit the conversion of androgens to estrogens. Oral administration of the compositions is by addition to the animal feed or water. The actual quantity of the aromatase inhibitor or inhibitors administered to the animals will vary over a wide range and can be adjusted to individual needs.

The novel aromatase inhibitor compositions may be added to a standard feed composition. The novel aromatase inhibitor compositions may be readily dispersed by mechanically mixing the aromatase inhibitor with the feedstuff, or with an intermediate formulation (premix) that is subsequently blended with other components to prepare the final feedstuff that is fed to the animal. The novel aromatase inhibitor compositions may also be added to carrier or filler materials for processibility, ease of handling and sale. Examples of suitable carriers include distillers fermentation solubles, feed grains, aminal, poultry and fish bi-products and meal, whey and other cellulosic carrier materials. A typical feed composition may contain from about 0.5 to about 1000 ppm aromatase inhibitor, preferably from about 5 to about 100 ppm aromatase inhibitor. The aromatase inhibitors may also be administered in animal drinking water, if they are soluble, at similar concentrations.

When the aromatase inhibitors are administered in time release formulations it is generally understood that the dosage will range from about 0.01 to about 10 mg/kg body weight. Timed release formulations are well known in the art.

The advantage of the present invention over the use of testosterone or anabolic steroids to enhance growth and feed conversion is that with the use of aromatase inhibitors the meat produced will not contain exogenous hormones.

The following example illustrates the present invention without, however, limiting the same thereto.

EXAMPLE 1

Effect Of Aromatase Inhibition On Weight Gain, Feed Conversion, Feed Consumption And Organ Weights Of Rats Male and female Sprague-Dawley rats were weaned and housed in individual cages in an air conditioned room (22° C.) with lighting from 0600–1800. Rodent chow and water were provided ad libitum. On the 30th day of age, females were divided into two treatment groups of twenty each according to body weight. One group of females was fed rodent chow containing 33.3 parts per million (ppm) of ±5-(p-Cyanophenyl)-5,6,7,8-tetrahydroimidazo[1,5-a]pyridine hydrochloride. The males and remaining group of females were fed a non-aromatase inhibitor control diet. Body weight and feed intake were monitored throughout the experiments. Females were inspected for vaginal opening after six weeks of age. Twenty-three days after aromatase inhibitor treatment, half of the medicated animals were switched to the non-aromatase control diet. All animals were killed two weeks later. The fresh weights of gastrocnemicus muscle, paramertic plus perirenal adipose tissues, ovaries and uteri were recorded. The significance of differences among treatments were determined by ANOVA and Newman-Keuls test.

Administration of ±5-(p-Cyanophenyl)-5,6,7,8-tetrahydroimidazo[1,5-a]pyridine hydrochloride to female rats significantly increased body weight gain (Table 1) and feed efficiency (Table 2) two weeks after treatment.

TABLE 1

EFFECTS OF AROMATASE INHIBITOR FEEDING ON WEIGHT GAIN IN RATS

| Treatment Days | Body Weight Gain, g | | |
|---|---|---|---|
| | Male (−)[a] | Female (−)[a] | Female (+)[a] |
| 7 | 57 ± 1.5 (20) | 42 ± 1.5 (20) | 46 ± 1.2 (20) |
| 15 | 120 ± 2.9 (20) | 74 ± 2.4 (20) | 96 ± 2.3 (20) (+30%)[b] |
| 23 | 178 ± 4.0 (20) | 98 ± 2.8 (20) | 142 ± 3.1 (19) (+45%)[b] |
| 30 | 224 ± 4.5 (20) | 116 ± 3.6 (20) | 190 ± 5.0 (9) (+64%)[b] |
| 37 | 263 ± 5.1 (20) | 134 ± 4.4 (20) | 321 ± 6.0 (9) (+72%)[b] |

[a](−) = non-medicated, (+) = medicated with 33.3 ppm of the aromatase inhibitor. Values equal mean ± standard error of the mean, (number of animals).
[b]significantly different from non-medicated female control (Newman-Keuls test $p < 0.05$).

Administration of the aromatase inhibitor significantly increased body weight gain, enhances weight gain. The magnitude of relative growth improvement increased with the length of time on treatment as the growth rate of normal females slowed down. The growth rate of continuously treated females was higher than untreated females and actually approached that of untreated males.

Feed efficiency was determined with female rats treated with aromatase inhibitor and compared to non-treated control animals, both male and female. Feed efficiency is enhanced by the treatment. Feed conversion efficiency is determined by dividing the amount of feed consumed by the body weight gain of individual animals. The results are shown in Table 2.

TABLE 2

EFFECTS OF AROMATASE INHIBITOR FEEDING ON FEED CONVERSION EFFICIECY IN RATS

| Treatment Days | Feed Consumption, g/Body Weight gain, g | | |
|---|---|---|---|
| | Male (−)[a] | Female (−)[a] | Female (+)[a] |
| 7 | 2.48 ± 0.05 (20) | 2.80 ± 0.09 (20) | 2.63 ± 0.06 (20) |
| 15 | 2.87 ± 0.06 (20) | 3.67 ± 0.10 (20) | 3.12 ± 0.06 (20) (15%)[b] |
| 23 | 3.22 ± 0.05 (20) | 4.50 ± 0.11 (20) | 3.55 ± 0.04 (19) (15%)[b] |
| 30 | 3.50 ± 0.05 (20) | 5.07 ± 0.12 (20) | 3.17 ± 0.06 (9) (27%)[b] |
| 37 | 3.77 ± 0.05 (20) | 5.51 ± 0.14 (20) | 3.93 ± 0.07 (9) (29%)[b] |

[a](−) = non-medicated, (+) = medicated with 3.33 ppm of the aromatase inhibitor. Values equal mean ± standard error of the mean, (number of animals).
[b]significantly different from non-medicated female control (Newman-Keuls test $p < 0.05$).

Administration of the aromatase inhibitor significantly increased feed efficiency. The feed efficiency of continuously treated females was greater than that of non-treated females and approached the efficiency of males.

All animals were killed two weeks after the final aromatase inhibitor treatment. The fresh weights of gastrocnemius muscle, parametric plus perirenal adipose tissues, ovaries and uteri were recorded. Aromatase inhibitor treatment increased the skeletal muscle size, adipose tissue mass and the tail length, indicating that the enzyme inhibitor promoted true growth of the animals.

Withdrawal of aromatase inhibitor from female animals resulted in a decrease of growth rate to the level of untreated controls within the first week of withdrawal.

During the second week after withdrawal the growth rate was reduced even further. Feed consumption during this period was maintained above the originally non-medicated female group. The rapid reversal of the growth effect upon drug withdrawal is consistent with the action of drugs which function as competitive enzyme inhibitors. There was a lag period between the commencement of drug treatment and the time when the growth responses became apparent. It appears that drug activity becomes effective when endogenous estrogen production begins to surge shortly before and after puberty.

EXAMPLE 2

Effects Of Aromatase Inhibitor On Growth And Feed Efficiency In Post-Pubertal Female Rats Female (five-week old) and male (four-week old) Sprague-Dawley rats were housed in individual cages in an conditioned room (22° C.) with lighting from 0600 to 1800. Purina rodent chow and water were provided ad libitum. After one week acclimation period, the female animals were divided into four treatment groups according to body weight. The animals were fed either non-medicated control ground chow or chow containing ±5-(p-Cyanophenyl)-5,6,7,8-tetrahydroimidazo[1,5-a]pyridine hydrochloride at 3, 10 or 33 ppm for 7 days. The male rats were divided into two groups, and fed the control diet or ±5-(p-Cyanophenyl)-5,6,7,8-tetrahydroimidazo[1,5-a]pyridine hydrochloride (33 ppm) for three weeks. Weight gain and feed consumption were monitored through the various times.

Feeding aromatase inhibitor to postpubertal female rats for only one week markedly increased body weight gain and the efficiency of feed conversion. Feed conversion efficiency is calculated by dividing the feed intake by the weight gain, with a smaller value showing better efficiency. The results are shown in the following table.

TABLE 3

Effects Of Aromatase Inhibitor Feeding On Growth And Feed Efficiency In Post-Pubertal Female Rats

| | Aromatase Inhibitor, ppm | | | |
|---|---|---|---|---|
| | 0 | 3 | 10 | 33 |
| Number of animals | 20 | 20 | 15 | 15 |
| Initial weight, g | 161 ± 1.7 | 161 ± 1.7 | 160 ± 1.9 | 160 ± 1.9 |
| Weight gain, g | 34 ± 1.5 | 40 ± 2.1 | 48 ± 1.7 | 49 ± 2.4 |
| % changes | | (20%)$^a$ | (41%)$^a$ | (43%)$^a$ |
| Feed conversion | 5.09 ± 1.8 | 4.34 ± 0.22 | 3.75 ± 0.07 | 3.68 ± 0.14 |
| % improvement over control | | (15%)$^a$ | (26%)$^a$ | (27%)$^a$ |

$^a$Percent change form non-medicated control (p > 0.01, Newman-Keuls test).

In male rats, aromatase inhibitor treatment from prepubertal through postpubertal periods slightly reduced the growth rate and feed efficiency.

What is claimed is:

1. A method (of) for enhancing weight gain and feed efficiency in an animal comprising administering to a healthy animal a weight gain enhancing and feed efficiency enhancing amount of an aromatase inhibitor.

2. The aromatase inhibitor of claim 1 wherein said aromatase inhibitor is selected from the group consisting of: 6-[(1H-imidazol-1-yl)phenylmethyl]-1 methyl-1H-benzotriazole, 6-[(4-chlorophenyl)(1H-1,2,4-triazol-1-yl)methyl]-1-methyl-1H-benzotriazole; 2,2-[5-(1H-1,2,4-triazol-1-ylmethyl)-1,3-phenylene]di(2-methylpropiononitrile), 2,2-[5-(imidazol-1-ylmethyl)-1,3-phenylene]-di(2-methylpropionitrile), 2-[3-(1-hydroxy-1-methylethyl)-5-(1H-1,2,4-triazol-1-ylmethylphenyl]-2-methylpropiononitrile, and 2,2-[5-dideuterio(1H-1,2,4-triazol-1-yl)methyl-1,3-phenylene]di (2trideuteriomethyl-3,3,3-(trideuteriopropiononitrile), and 2,2-[5-dideuterio(1H-1,2,4-triazol-1-ylmethyl-1,3-phenylene)di(2-methylpropiononitrile); 1,1-dimethyl-8-(1H-1,2,4-triazol-1-ylmethyl)-2(1H)-naphtho[2,1-b]furanone, 1,2-dihydro-1,1-dimethyl-2-oxo-8-(1H-1,2,4-triazol-1-ylmethyl)naphtho-[2,1-b]furan-7-carbonitrile, 1,2-dihydro-1,1-dimethyl-2-oxo-8-(1H-1,2,4-triazol-1-ylmethyl)-naphtho[2,1-b]furan-7-carboxamide, and 1,2-dihydro-1,1-dimethyl-2-oxo-8-[di(1H-1,2,4-triazol-1 yl)-methyl]naphtho[2,1-b]furan-7-carbonitrile; 2-(4-chlorobenzyl)-2-fluoro-1,3-di(1,2,4-triazol-1-yl)propane, 2-fluoro-2-(2-fluoro-4-chlorobenzyl)-1,3-di(1,2,4-triazol-1-yl)propane, 2-fluoro-2-(2-fluoro-4-trifluoromethylbenzyl)-1,3-di(1,2,4-triazol-1-yl)propane, 3-(4-chlorophenyl)-1-(1,2,4-triazol-1-yl)-2-(1,2,4-triazol-1-ylmethyl)butan-2-ol, 2-(4-chloro-α-fluorobenzyl)-1,3-di(1,2,4-triazol-1-yl)propan-2-ol, 2-(4-chlorobenzyl)-1,3-bis(1,2,4-triazol-1-yl)propane, 4-[2-(4-chlorophenyl)-1,3-di(1,2,4-triazol-1-ylmethyl)ethoxymethyl]-benzonitrile, 1-(4-fluorobenzyl)-2-(2-fluoro-4-trifluoromethylphenyl)-1,3-di(1,2,4-triazol-1-yl)propanylmethyl)ethoxymethyl]-benzonitrile, 1-(4-fluorobenzyl)-2-(2-fluoro-4-trifluoromethylphenyl)-1,3-di(1,2,4-triazol-1-yl)propan-2-ol, 2-(4-chlorophenyl)-1-(4-fluorophenoxy)-1,3-di(1,2,4-triazol-1-yl)propan-2-ol, 1-(4-cyanobenzyl)-2-(2,4-difluorophenyl)-1,3-di(1,2,4-triazol-1-yl)-propan-2-ol and 2-(4-chlorophenyl)-1-phenyl-1,3-di(1,2,4-triazol-1-yl)-propan-2-ol; 5-bis(4-chlorophenyl)methylpyrimidine; α,α-bis(4-chlorophenyl)-2-pyrazinemethanol; N-(2,4-difluorophenyl)-N-benzyl-3-pyridinemethanamine and N-(2-chlorophenyl-α-(4-fluorophenyl)-3-pyridinemethanamine; 1-(10,11-dihydro-5H-dibenzo[a,d]cyclohepten-5-yl)-1H-imidazole and 1-(9H-fluoren-9-yl)-1H-imidazole; 3-bis(4-chlorophenyl)-3-methylpyridine and α,α-bis(4-chlorophenyl)-3-pyridinemethanol; 5H-5-(4-cyanophenyl)-6,7-dihydropyrrolo[1,2-c]imidazole and 5H-5-(4-cyanophenyl)-6,7,8,9-tetrahydroimidazo[1,5-a]azepine; 5-[(1H-imidazol-1-yl)phenylmethyl]-2-methyl-1H-benzimidazole and 5-[(3-chlorophenyl)(1H-imidazol-1-yl)-methyl]-1H-benzimidazole; (Z)-α-(1,2,4-triazol-1-ylmethyl)stilbene-4,4'-dicarbonitrile, (Z)-4'-chloro-α-(1,2,4-triazol-1-ylmethyl)stilbene-4-carbonitrile, (Z)-α-(1,2,4-triazol-1-ylmethyl)-4'-(trifluoromethyl)stilbene-4-carbonitrile, (E)-β-fluoro-α-(1,2,4-triazol-1-ylmethyl)-stilbene-4,4'-dicarbonitrile, (Z)-4'-fluoro-α-(imidazol-1-ylmethyl)stilbene-4-carbonitrile, (Z)-2',4'-dichloro-α-(imidazol-1-ylmethyl)stilbene-4-carbonitrile, (Z)-4'-chloro-α-(imidazol-1-ylmethyl)stilbene-4-carbonitrile, (Z)-α-(imidazol-1-ylmethyl)stilbene4,4'-dicarbonitrile, (Z)-α-(5-methylimidazol-1-ylmethyl)stilbene-4,4'-dicarbonitrile, and (Z)-2-[2-(4-cyanophenyl)-3-(1,2,4-triazol-1-yl)propenyl]pyridine-5-carbonitrile; (1R*,2R*)-6-fluoro-2-(4-fluorophenyl)-1,2,3,4-tetrahydro-1-(1H-1,2,4-triazol-1-ylmethyl)naphthalene, (1R*,2R*)-6-fluoro-2-(4-fluorophenyl)-1,2,3,4-tetrahydro-1-(1H-imidazolylmethyl)-naphthalene, (1R*,2R*)-and (1R*,2S*)-2-(4-fluorophenyl)-1,2,3,4-tetrahydro-1-(1H-1,2,4-triazol-1-ylmethyl)naphthalene-6-carbonitrile, (1R*,2R*)- and (1R*,2S*)-2-(4-fluorophenyl)-1,2,3,4-thetahydro-1-(1H-imidazolylmethyl)naphthalene-6-carbonitrile, (1R*,2R*)- and (1R*,2S*)-1,2,3,4-tetrahydro-1-(1H-1,2,4-triazol-1-ylmethyl)naphthalene-2,6-dicarbonitrile, (1R*,2R*)- and (1R*,2S*)-1,2,3,4-tetrahydro-1-(1H-imidazol-1-ylmethyl)naphthalene-2,6-dicarbonitrile, and (1R*,2S*)-2-(4-fluorophenyl)-1,2,3,4-tetrahydro-1-(5-methyl-1H-imidazolylmethyl)naphthalene-6-carbonitrile; 8-chloro-5-(4-chlorophenyl)-5H-indeno[1,2-d]pyrimidine; 5-bis (4-chlorophenyl) methylpyrimidine; 10-(2-propynyl)-estr-4-ene-3,17-dione; 6-[(4-chlorophenyl)(1H-1,2,4-triazol-1-yl)methyl]-1-methyl-1H-benzotriazole; 1-methylandrosta-1,4-dien-3,17-dione; 3-ethyl-3-(4-pyridyl)piperidine-2,6-dione; 4-hydroxyandrostene-3,17-dione; 4-(5,6,7,8-tetrahydroimidazo[1,5-a]pyridin-5-yl)benzonitrile; 6-methyleneandrosta-1,4-diene-3,17-dione, 4-aminoadrostan-1,4,6-trien-3,17-dione and 4-aminoandrosta-4,6-diene-3,17-dione; 3-(1H-imidazol-1-ylmethyl)-2-methyl-1H-indole-1-propanoic acid; 5-[3-chlorophenyl)(1H-imidazol-1-yl)methyl]-1H-benzimidazole; 10β-thiiranylestr-4-ene-3,17-dione and 10β-oxiranylestr-4-ene-3,17-dione; 3-ethyl-3-(4-pyridyl)piperidine-2,6-dione; 3-(4-aminophenyl)-3-ethyl-pyrrolidine-2,5-dione; 1-(7-carboxyheptyl)imidazole; 1,1-dimethyl-8-(1H-1,2,4-triazol-1-ylmethyl)-2(1H)-naphtho[2,1-b]furanone (1a); ±5-(p-cyanophenyl)-5,6,7,8-tetrahydroimidazo[1,5-a]pyridine hydrochloride; 1,4,6-androstatriene-3,17-dione; and bis-(p-cyanophenyl)-imidazo-1-ylmethane hemisuccinate and acid addition salts thereof.

3. The aromatase inhibitor of claim 2 wherein the said aromatase inhibitor is ±5-(p-cyanophenyl)-5,6,7,8-tetrahydroimidazo[1,5-a]pyridine hydrochloride.

4. A method for enhancing weight gain and feed efficiency in meat animals comprising administering to a health meat animal a weight gain enhancing and feed efficiency enhancing amount of an aromatase inhibitor.

* * * * *